(12) United States Patent
Thorpe

(10) Patent No.: US 6,454,952 B1
(45) Date of Patent: Sep. 24, 2002

(54) FLUID STERILIZATION APPARATUS

(75) Inventor: George W. Thorpe, Vancouver (CA)

(73) Assignee: International Water-Guard Industries, Inc., British Columbia (CA)

( * ) Notice: Subject to any disclaimer, the term of this patent is extended or adjusted under 35 U.S.C. 154(b) by 0 days.

(21) Appl. No.: 09/762,246

(22) PCT Filed: Jun. 5, 2000

(86) PCT No.: PCT/CA00/00674

§ 371 (c)(1),
(2), (4) Date: Jul. 2, 2001

(87) PCT Pub. No.: WO00/75081

PCT Pub. Date: Dec. 14, 2000

(30) Foreign Application Priority Data

Jun. 4, 1999 (CA) .............................................. 2273745

(51) Int. Cl.⁷ .................................................. C02F 1/32
(52) U.S. Cl. ..................... 210/748; 210/512.1; 250/437; 250/438
(58) Field of Search .................................. 210/748, 252, 210/259, 260, 282, 512.1, 95; 422/186.3; 250/432 R, 437, 438

(56) References Cited

U.S. PATENT DOCUMENTS

| | | | |
|---|---|---|---|
| 4,008,045 A | * | 2/1977 | Free |
| 4,769,131 A | * | 9/1988 | Noll et al. |
| 5,069,885 A | * | 12/1991 | Ritchie |
| 5,393,419 A | | 2/1995 | Tiede et al. .................. 210/192 |
| 5,540,848 A | * | 7/1996 | Englehard |
| 5,675,153 A | * | 10/1997 | Snowball |

FOREIGN PATENT DOCUMENTS

| | | | |
|---|---|---|---|
| DE | 3117473 A | | 11/1982 |
| DE | 4317343 | * | 5/1993 |
| EP | 0508338 | * | 4/1992 |
| EP | 0616975 A | | 9/1994 |

* cited by examiner

Primary Examiner—David A. Simmons
Assistant Examiner—Fred Prince
(74) Attorney, Agent, or Firm—Moore & Van Allen PLLC; Michael G. Johnston

(57) ABSTRACT

Apparatus for treating water or other fluid with radiant energy from an ultraviolet lamp includes a helical shaped input fluid flow guide or helical ramp disposed at or near one end an elongated annular chamber around the lamp. The guide or ramp serves to impart input spiral flow momentum to the fluid upon entry to the chamber. A corresponding output fluid flow guide or helical ramp may be disposed at or near the opposed end of the chamber to impart output spiral flow momentum to the fluid as it approaches discharge from the chamber. Spiral flow serves to extend the time that the fluid is exposed to ultraviolet light and thereby increases the probability that any microbiological contaminants present in the fluid will be killed. The use of helical shaped guides or ramps better serves to establish such a flow in circumstances where the available fluid pressure is relatively low.

11 Claims, 3 Drawing Sheets

FLUID STERILIZATION APPARATUS

FIELD OF THE INVENTION

This invention relates to fluid sterilization apparatus of the type for treating potable water or other fluids with radiant energy from an ultraviolet lamp.

BACKGROUND TO THE INVENTION

It is well known that the quality of potable water varies widely from city to city around the world. Indeed, the quality can vary significantly from place to place within a given city. To address this issue, numerous water treatment systems have been designed for domestic home use: A typical system may include a water filter for removing particulates and organic contaminants from the water, an ultraviolet lamp for irradiating the water with ultraviolet energy to kill contaminants in the water, a subsystem for operating and monitoring the operation of said system, and structures for housing such components. Often, such systems are designed to sit on a countertop in the user's home where they are connected to a public utility or other municipal water supply. For example, see U.S. Pat. No. 5,698,091 (Kuennen et al.) granted on Dec. 16, 1997.

It is also well known that the quality of potable water carried on board passenger vehicles such as aircraft, trains and ships can vary significantly: for example, see Weisel, Al "*Dirty Water—Our investigation into water on airplanes will make you think before your drink*", Travel & Leisure, December 1998, pages 139–142. In the case of such vehicles, the quality of potable water will depend not only on the source from whence the water came, but also on the integrity of on board storage tanks and supply lines where contamination may result from microorganism growth or biofilm buildup.

Accordingly, just as it is desirable to provide for the treatment of potable water in the home, it is desirable to provide for the treatment of potable water carried on board vehicles. However, the working environment to be found on board a vehicle may differ significantly from that to be found in the home. A water treatment system or components thereof that function reliably and well in the home may not function at all well in a mobile working environment.

As will now be described, the present invention focuses on one such area of limitation. More particularly, it focuses on sterilization apparatus that may be used in the treatment of water or other fluids with radiant energy from an ultraviolet lamp.

As the prior art reveals, such apparatus commonly includes an outer housing having first and second ends, a hollow cylindrical portion extending between such ends, and a coaxially aligned inner housing, the latter of which is designed to hold an ultraviolet lamp. The housings are sized to define an elongated annular region or chamber between the housings. As fluid flows from an inlet at one end of the chamber to an outlet at the opposed end, it is exposed to ultraviolet energy that emits from the lamp into the annular chamber through a wall of the inner housing which transmits ultraviolet light.

In such apparatus, the desirability of maintaining the fluid for an extended period of time within the field of view of the radiation is well known. If microbiological contaminants are present, then the probability of killing such contaminants will be enhanced. Consequently, various means have been devised to achieve this result.

For example, U.S. Pat. No. 4,008,045 (David Free) granted on Feb. 15, 1977, describes an ultraviolet sterilizer that includes a diffuser plate through which fluid in the an annular chamber must pass as it flows from an inlet at one end of the chamber to an outlet at the other. The diffuser serves to impart turbulence and a spiral flow to the fluid thereby increasing the distance that a given control volume of fluid will travel while flowing from the diffuser to the chamber outlet.

However, it has been found that the pressure drop or head loss that occurs across such diffusers is relatively high. This can be disadvantageous if the fluid supply pressure is concurrently limited and it is desired to maintain a minimal water flow rate. More particularly, it may be observed that in a home use environment the input water pressure from a public utility or municipal water source typically may be of the order of 100 psig. If so, then the pressure drop across a diffuser in an ultraviolet sterilization chamber tends not to be an issue. In contrast, and although there may be some exceptions, the pressure produced by a water pump on a passenger aircraft may typically be only 45 psig or lower—sometimes as low as 20 psig. For a desired water flow rate through an ultraviolet sterilizer, such low pressures may preclude the use of a diffuser or, alternately, may preclude the use of other water treatment devices which themselves cause a pressure drop (e.g. a water filter) in the path of water flow.

As a further example, U.S. Pat. No. 4,141,686 (Lewis) granted on Feb. 27, 1979, describes an ultraviolet sterilizer that includes a fin which imparts turbulence to water as it flows into the annular chamber of the sterilizer. While it may be remarked that the pressure drop induced by the fin described by Lewis is likely to be minimal, and while it may also be remarked that turbulence is desirable, it must also be remarked that Lewis' fin is not well adapted to induce a desirable spiral flow. Apart from turbulence, a significant volume of the water that enters the annular chamber may follow a relatively short path (sometimes referred to as a short circuit path) rather than a spiral path to the chamber outlet. Thus, the water's exposure to ultraviolet radiation is undesirability limited.

As a more recent example, Kuennen et al., supra, describe a diverter plate and baffle arrangement that serves to impart a spiral flow within the annular chamber of an ultraviolet sterilizer. However, it is noted that they specifically contemplate a high pressure home use environment, and it is anticipated that a significant pressure drop would occur, particularly across the baffle which may be compared with the diffuser of Free. The diverter plate and baffle arrangement is described in more detail in U.S. Pat. No. 5,393,419 (Tiede et al who are part of Kuennen et al.) granted on Feb. 28, 1995.

Kuennen et al. also point out that other embodiments may by used to impart a spiral flow to water passing through their annular chamber. They indicate that a spiral glass or polymeric (e.g. TEFLON®) tube may be coiled about the ultraviolet lamp with a spiral pitch from the water inlet end of the chamber to the water outlet end, and that such material has adequate ultraviolet transmissibility to achieve excellent kill rates. However, even assuming that ultraviolet transmissibility is normally adequate, there are disadvantages. Firstly, there would be a relatively high pressure drop across the coil by reason of the added surface area presented by the surfaces of the coil over the length of the coil. Secondly, it has to be recognized that sediment can build up on all surfaces over which water flows. In a case where a coil as suggested by Kuennen et al. is used, this would include not only the wall surfaces of the annular chamber, but also on the surfaces defining the coil. Sediment build up on the walls of the coil could very well impair the transmissibility of coil material that otherwise might demonstrate adequate ultraviolet transmissibility.

Accordingly, a primary object of the present invention is to provide new and improved apparatus for treating water or other fluid with radiant energy from an ultraviolet lamp in circumstances where the available fluid pressure is relatively low.

SUMMARY OF THE INVENTION

In a broad aspect of the present invention, there is provided apparatus for treating water or other fluid with radiant energy from an ultraviolet lamp, such apparatus comprising an outer housing comprising first and second ends and an elongated hollow cylindrical portion extending between the ends peripherally around a longitudinal axis of the cylindrical portion, and a hollow cylindrical inner housing for housing the ultraviolet lamp. The inner housing is supported by the ends of the outer housing and extends coaxially within the cylindrical portion of the outer housing so as to define an elongated annular chamber between the housings. At least a substantial portion of the length of the inner housing is formed from material, preferably quartz, which is sufficiently transmissible to permit ultraviolet energy radiating from the lamp to pass through the inner housing into the chamber and thereby irradiate fluid flowing through said chamber. The apparatus further comprises a fluid inlet conduit extending through the first end of the outer housing from a fluid inlet port to the annular chamber, and a fluid outlet conduit extending through the second end of the outer housing from the annular chamber to a fluid outlet port. The fluid inlet conduit serves to receive fluid from an external source and to direct such fluid to the annular chamber. Conversely, the fluid outlet conduit serves to discharge fluid from the annular chamber. Further, the apparatus includes a helical shaped input fluid flow guide or helical ramp for imparting input spiral flow momentum to fluid upon entry to the annular chamber from the fluid inlet conduit. Preferably, it also includes a corresponding helical shaped output fluid flow guide or helical ramp for imparting output spiral flow momentum to fluid approaching discharge from the chamber through the fluid outlet conduit.

The input fluid flow guide or ramp is disposed within the annular chamber and extends longitudinally therein from the first end of the outer housing for a relatively short distance. Conversely, the output fluid flow guide or ramp, which is also disposed within the annular chamber but relatively far from the input flow guide or ramp, extends longitudinally from the second end of the outer housing for a relatively short distance.

In contrast to diffusers, baffles, or helical shaped guides that extend continuously for substantially the full length of an annular chamber, all of which may offer relatively high resistance to fluid flow and may present other disadvantages, the helical shaped guides as specified herein offer relatively low resistance. Yet, it has been found that they can serve to impart a significant and desirable spiral flow momentum to the fluid.

Preferably, a helical guide or ramp will have an inner radius substantially corresponding to an outer radius of the inner housing and an outer radius substantially corresponding to an inner radius of the outer housing. Otherwise some fluid may flow around the sides of the guide or ramp with little or no spiral momentum.

The foregoing and other features of the present invention will now be described with reference to the drawings.

DETAILED DESCRIPTION OF PREFERRED EMBODIMENT

Figure 1:
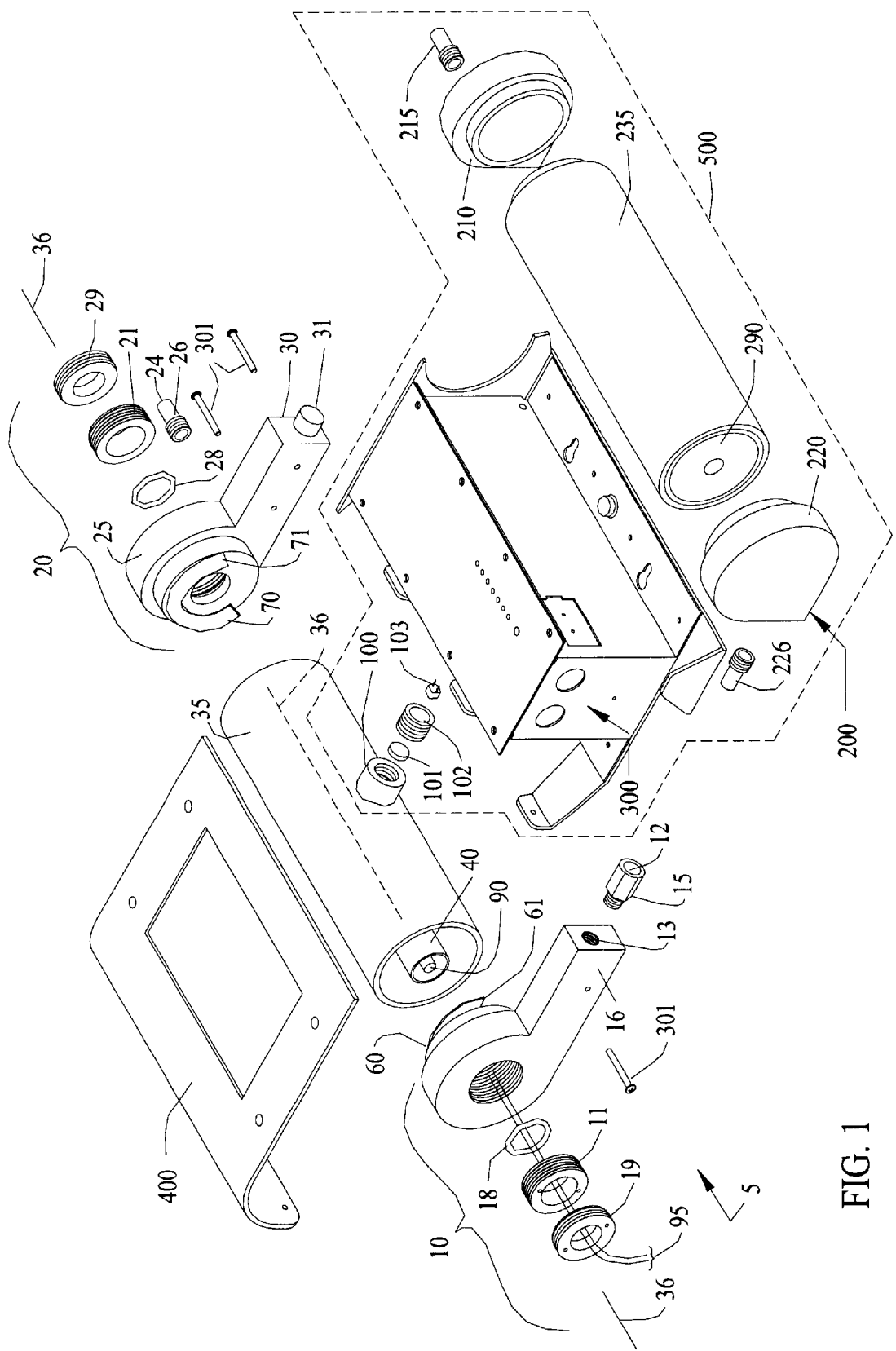
FIG. 1 is a partially exploded perspective view of a water treatment system that incorporates apparatus in accordance with the present invention for treating fluid with radiant energy from an ultraviolet source.

FIG. 1 illustrates a preferred embodiment of the present invention when configured to integrate with and form part of a potable water treatment system that includes not only apparatus generally designated 5 for treating water with radiant energy from an ultraviolet lamp, but also apparatus generally designated 200 for filtering such water before it is exposed to ultraviolet light. Further, the system as shown includes a housing assembly generally designated 300 to hold electrical and electronic components and circuitry for operating and monitoring the operation of the system. As well, the system includes a cover 400 which normally overlies lamp apparatus 5, filter apparatus 200, and housing assembly 300.

It is to be understood that cover 400 and generally that part of the system appearing within broken border 500, including filter apparatus 200 and housing assembly 300, is not considered to be part of the present invention. They are illustrated in the drawings only to better explain the rationale for the particular configuration of lamp apparatuss which appears in the drawings. More particularly, the overall system is one which is designed and configured for operation on board an aircraft under conditions of relatively low water pressure, and the preferred embodiment described herein is designed as an integral part of that system. However, conditions of low pressure may be found elsewhere. As well, although water filtration is often desirable, it will be appreciated that the present invention does not require such filtration. Accordingly, in other applications, lamp apparatus 5 may assume differing configurations.

Figure 2:
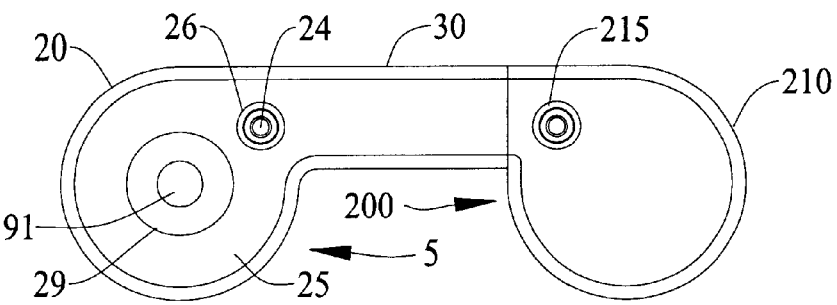
FIG. 2 is a top view of a portion of the system shown in FIG. 1 when in an assembled condition, the apparatus which incorporates the present invention lying generally to the left.

Lamp apparatus 5 comprises an outer housing which includes first and second ends or end caps 10, 20, and an elongated cylindrical portion 35 that extends between such ends and peripherally around axis 36, the latter of which aligns with the cylindrical or longitudinal axis of cylindrical portion 35. During assembly, ends 10, 20 are sliding received by cylindrical portion 35 and then glued in place as shown in FIG. 2. Further lamp apparatus 5 comprises a hollow cylindrical sheath or inner housing 40.

Inner housing 40 is supported by housing ends 10, 20 by means of sheath retainers 11, 21 which are threadingly engageable with the main body of the ends, and which are considered to form part of such ends. Inner housing 40 extends coaxially within cylindrical portion 35 so as to define an elongated annular chamber 50 between the inner and outer housings.

Figure 3:
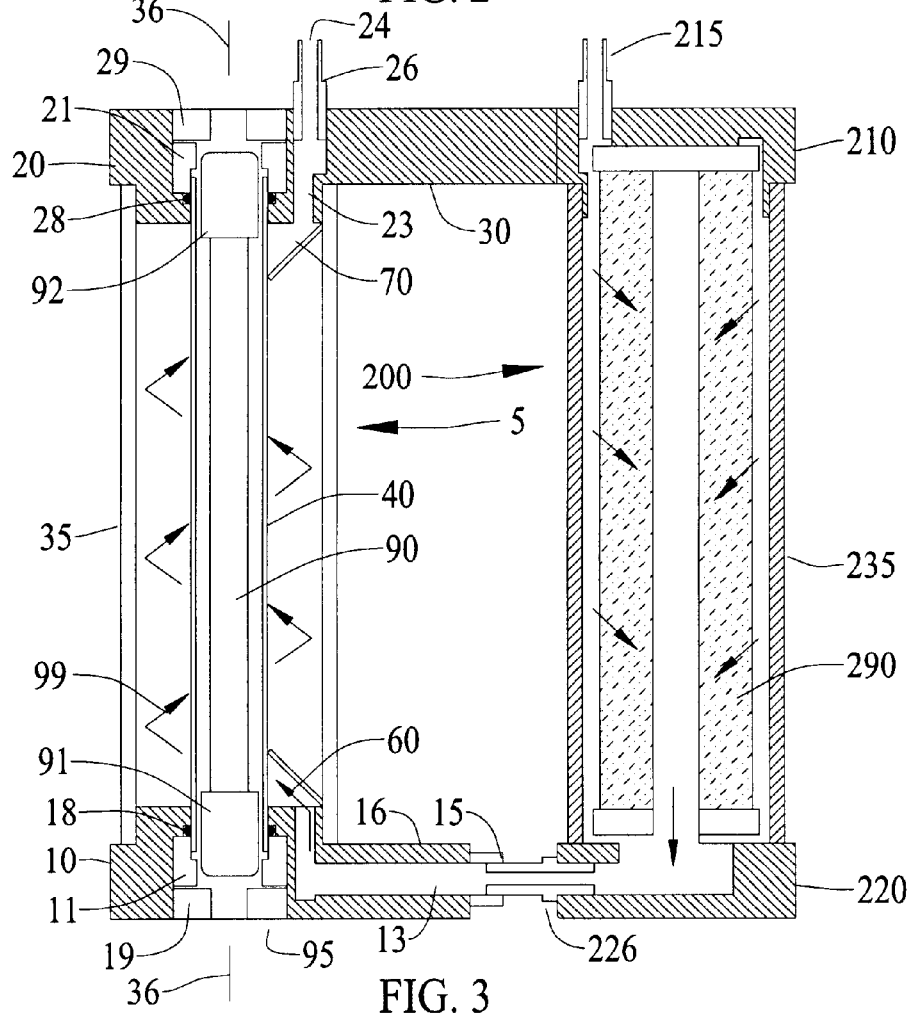
FIG. 3 is a sectional elevation view of a portion of the system shown in FIG. 1 when in an assembled condition, the apparatus which incorporates the present invention lying generally to the left.

An ultraviolet lamp 90 is housed by inner housing 40, and extends longitudinally therein between ceramic end caps 91, 92 (see FIG. 3). When in place, lamp 90 is secured at opposed ends by lamp retaining plugs 19, 29 which are threadingly engageable with the main body of ends 10, 20 respectively, and which are considered to form part of such ends. Power input to the lamp is provided through wires 95 which may receive power from any appropriate power source and power supply circuitry.

It will be noted that plugs 19, 29 are not solid plugs; they are ring shaped to leave an air opening through their centers. Likewise, it will be noted that there is an annular air space between sheath retainers 11, 21 and end caps 91, 92. Also, there is an annular air space between caps 91, 92 and the inner wall of housing 40. All of such air spaces and openings serve to facilitate the air cooling of the lamp 90 when it is in place and in operation.

Figure 5:
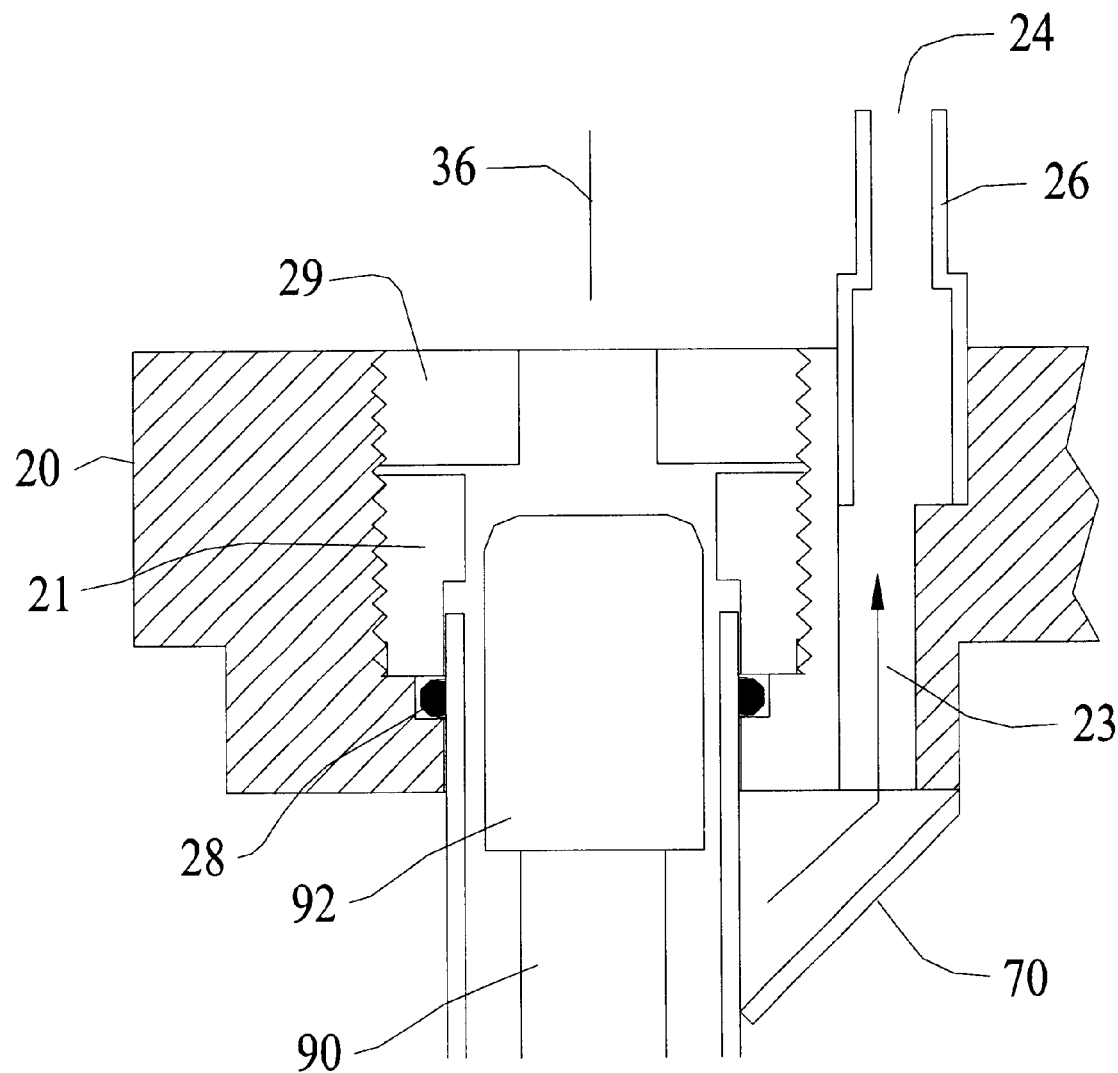
FIG. 5 is an enlarged cut-a-way view of the upper left corner of FIG. 3.

Lamp 90 is sealed from annular chamber 50 by means of elastomeric "O" rings 18, 28 which are respectively associated with ends 10, 20. As best seen in FIG. 5, ring 28 is normally compressed between housing 40, an inner flange end 20, and retainer 21, thereby forming a water tight seal. Although not depicted in detail, ring 18 in cooperation with retainer 11 forms a seal at end 10 in the same manner.

The main bodies of ends 10, 20 and retainers 11, 19, 21 and 29 may all be fabricated from polyvinyl chloride (PVC) plastic. Cylindrical portion 35 is preferably formed from chlorinated PVC which has about 50% more strength as well as fire retardant properties.

Inner housing 40 is formed from a material sufficiently transmissible to permit ultraviolet energy radiating from lamp 90 to pass through housing 40 and flood chamber 50 with such energy. Then, as water flows through chamber 50 in the manner described below, it is irradiated with the ultraviolet energy. Preferably the material forming inner housing 40 is a high purity quartz material. As is well known, such material transmit ultraviolet energy very well.

Figure 4:
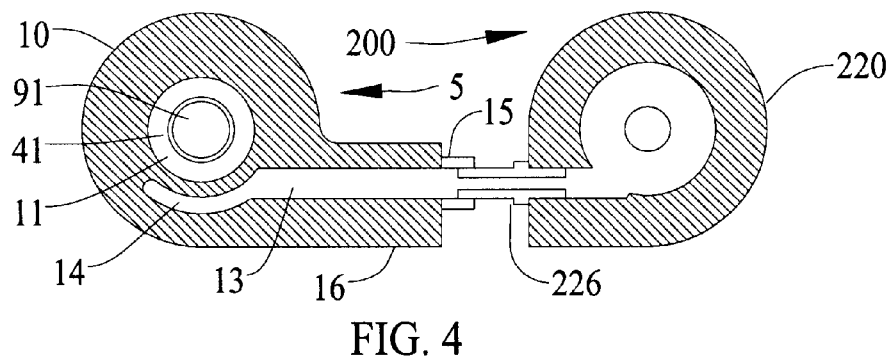
FIG. 4 is a sectional view from below of a portion of the system shown in FIG. 1 when in an assembled condition, the apparatus which incorporates the present invention lying generally to the left.

As best seen in FIGS. 1, 3 and 4, a water inlet conduit 13 extends through end 10 from a water inlet port 12 to chamber 50. As shown in FIG. 4, conduit 13 includes an annular race 14 (which race is of progressively decreasing depth). Inlet port 12 appears in a water inlet fitting 15 which forms part of end 10 and which is normally threadingly engaged with arm 16 of end 10. More specifically, fitting 15 as shown is the female portion of a quick connect coupling that enables the apparatus 5 to be releasably connected in water flow communication with an external source of water. In the embodiment shown, the immediate source of external water received via fitting 15 is the output from filter apparatus 200 through fitting 226. It necessarily follows that fitting 226 is a male counterpart of female fitting 15.

As best seen in FIG. 3 and also FIG. 5, a water outlet conduit 23 extends through end 20 from chamber 50 to a water outlet port 24. Outlet port 24 appears in a water outlet fitting 26 which forms part of end 20 and which is normally threadingly engaged with the circular body portion 25 of end 20. More specifically, fitting 26 as shown is the male portion of a quick connect coupling that enables the apparatus to be releasably connected in water flow communication with a water line (not shown) leading to a tap (also not shown) from which a user may draw water. Of course, it will be understood that the water line should begin with a corresponding female fitting (not shown). In practice, it will likely be convenient for fitting 26 to be the same kind of fitting as fitting 226, and for the fitting at the beginning of the water line leading to the tap to be the same kind of fitting as fitting 15.

Referring now to FIGS. 1 and 3, it will be seen that the apparatus further includes a helical shaped input fluid flow guide or ramp 60 disposed within chamber 50 and extending longitudinally therein from end 10 for a relatively short distance. Further, it will be seen that the apparatus includes a helical shaped output fluid flow guide or ramp 70 also disposed within chamber 50 and extending longitudinally therein from end 20 for a relatively short distance. These features are at the focus of the present invention.

Each ramp extends for about one helical revolution. In relation to the overall length of cylindrical portion 35, it will be noted that the longitudinal extension of ramps 60, 70 as determined by their helical pitch is relatively short, and that there is a substantial distance between the ramps. Thus, a substantial part of the field of view that ultraviolet lamp 90 has of chamber 50 is unimpeded by the ramps.

As best seen in FIG. 1, ramp 70 is secured by a pin 71 to end 20. Although not shown, ramp 60 is likewise secured to end 10.

Just as end portion 10 includes a transversely extending arm 16, it will be observed that end 20 includes a transversely extending arm 30. These arms are not essential to the present invention and both ends 10, 20 could be reconfigured to have a more compact cylindrical cap form. However, the ends are illustrated with the present embodiment because they serve to integrate apparatus 5 with the overall water treatment system illustrated in FIG. 1.

Briefly, end 10 of lamp apparatus 5 connects via fitting 15 in direct water flow communication via fitting 226 with the output of corresponding end 220 of filter apparatus 200. Concurrently, end 20 of lamp apparatus 5 mechanically connects with opposite end 210 of filter apparatus 200. With respect to the latter connection, stub 31 at the distal end of arm 30 (see FIG. 1) is slidingly received by a corresponding recess (not shown) in end 210 of filter apparatus 200. End 210 of filter apparatus 200 includes a water inlet fitting 215. Preferably, this fitting is essentially the same type of male fitting as fittings 26 and 226.

When connections are made in the manner indicated in FIGS. 2 to 4, the net result is that arms 16, 30 of lamp apparatus 5 serve to provide mechanical support for filter apparatus 200. In the system shown in FIG. 1, this support is enhanced by housing assembly 300 which not only serves to cradle and support lamp apparatus 5 and filter apparatus 200 when they are connected, but also provides a structure to which arms 16 and 30 of lamp apparatus 5 may be bolted by means of bolts such as bolts 301. Structural integrity is further enhanced by cover 400, preferably made from fire retardant plastic. Cover 400 includes a curvate end and a flat upper plate portion which extends away from the curvate end. The curvate end abuts and conforms with the curvature of cylindrical portion 35 and is normally bolted to each of three support leaves (see FIG. 1) that project upwardly and outwardly from the base of housing assembly 300. The flat upper plate portion of cover 400 extends over and is bolted to the top of housing assembly 300, and marginally extends over filter apparatus 200. The result is a well integrated structure which is resistant to shock and vibration conditions that may be encountered on board an aircraft.

In order to facilitate the replacement of water filter 290, cover 400 does not wrap around cylindrical portion 235 of filter apparatus 200 in the manner of cylindrical portion 35 of lamp apparatus 5. If filter replacement is required, it is merely necessary to release the engagement between fitting 226 and fitting 15 and pull the entire filter apparatus laterally away from housing assembly 300. Concurrently, end 210 of filter apparatus 200 slides out of engagement with stub 31 of lamp apparatus 5. Then, filter replacement is made possible by removing end 220 of filter apparatus 200, which end is normally threadingly engaged with cylindrical portion 235. (Opposed end 210 is normally secured by glue.)

The replacement of lamp 90 is achieved by unthreading retainers 19 and 11 from end 10 of lamp apparatus 5, removing the lamp longitudinally along axis 36, disconnecting wires 95, and then installing a new lamp.

In operation, pressurized potable water having entered the annular region of filter apparatus 200 through fitting 215, and been filtered by hollow core filter 290, then enters the lamp apparatus 5 at end 10 through inlet port 12. The input flow first follows water inlet conduit 13 which leads to and includes annular race 14, from which the flow exits into the path defined by helical ramp 60. Ramp 60 directs the incoming flow in a clockwise spiral path and thereby imparts angular or input spiral flow momentum to the water. As the flow leaves ramp 60 in chamber 50 and moves toward end 20, it thus begins to traverse the length of the chamber in a spiral path as indicated by arrows 99 in FIG. 3.

Of course, the input spiral flow is desirable because it serves to increase the length of time that water will be exposed to ultraviolet light from lamp 90. It may also be noted that trailing edge 61 of ramp 60 (see FIG. 1) may induce a degree of desirable turbulence in the flow. More particularly, in a related test where colored dye was injected into a water flow, there was visible flow separation or eddying turbulence as water passed over a trailing edge similar to edge 61. However, it is presently not possible to quantify the degree of turbulence or what conditions should prevail to ensure at least some turbulence.

While the initial spiral flow imparted by ramp 60 is desirable in and of itself, and while ramp 60 will serve a primary object of the present invention with or without the presence of ramp 70, the combined presence of ramp 70 serves the primary object to an enhanced degree. More particularly, as a water flow approaches end 20 and ultimate discharge from chamber 50, ramp 70 constrains the flow to move in a spiral path. Perhaps akin to a whirlpool effect, this constraint serves to induce a spiral motion and impart an output spiral flow momentum to the water before it reaches ramp 70.

Along ramp 70, the output flow is directed in a continuing clockwise spiral path to outlet conduit 23. The water, now having been treated with ultraviolet radiation from lamp 90, then leaves the apparatus at end 20 through outlet port 24 and is available for drinking or other use.

In a test apparatus wherein a chamber 50 was defined between an inner housing 40 having an outside diameter of about 1 inch and a cylindrical portion 35 having an inside diameter of about 2.5 inches, and again using colored dye for the purpose of observation, it was observed that about 8 to 10 fluid spiral revolutions occurred between a ramp 60 and a ramp 70, each having a helical pitch of about 3 revolutions per inch. The overall chamber length was about 8.5 inches. This observation was made with a flow rate of about 1 U.S. gallon per minute which was achieved with a head pressure of 35 to 40 psig.

Of course, apparatus in accordance with the present invention may incorporate features that are not part of the invention, but which may be considered desirable. By way of example, FIG. 1 illustrates a portion of a means for sensing the output of ultraviolet lamp 90. This means includes a view port 100 leading to a circular wall opening (not shown) through the wall of cylindrical portion 35, a quartz disc 101, a threaded sleeve 102 and an ultraviolet sensor 103. Disc 101 has a diameter larger than the circular wall opening and is held in place over the opening to provide both a seal against water in chamber 50 and a window through which energy emitting from lamp 90 can be sensed and monitored by sensor 103 with known sensing and monitoring circuitry. Such sensing and monitoring circuitry is not shown. However, in the water treatment system illustrated in FIG. 1, the bulk of such circuitry would normally be carried in housing assembly 300. Likewise, appropriate power supply circuitry, both for lamp 90 and for any sensing and monitoring circuitry, would normally be carried in housing assembly 300.

While the invention has been described in detail in relation to apparatus for treating potable water, it is to be understood that the invention is not limited to the treatment of water. It may be used to treat other fluids through which ultraviolet energy can permeate in an effective manner.

Various modifications and changes to the embodiment that has been described can be made without departing from the scope of the present invention, and will undoubtedly occur to those skilled in the art. The invention is not to be construed as limited to the particular embodiment and should be understood as encompassing all those embodiments that are within the spirit and scope of the claims that follow.

What is claimed is:

1. Apparatus for treating fluid with radiant energy from an ultraviolet lamp, said apparatus comprising:
   (a) an outer housing comprising first and second ends and an elongated hollow cylindrical portion extending between said ends peripherally around a longitudinal axis of said cylindrical portion;
   (b) a hollow cylindrical inner housing for housing said lamp, said inner housing being supported by said ends and extending coaxially within said cylindrical portion of said outer housing so as to define an elongated annular chamber between said housing, at least a substantial portion of the length of said inner housing being formed from material sufficiently transmissible to permit ultraviolet energy radiating from said lamp to pass through said inner housing into said chamber and thereby irradiate fluid flowing through said chamber;
   (c) a fluid inlet conduit extending through said first end from a fluid inlet port to said chamber for receiving said fluid from an external source of fluid and directing said fluid to said chamber;
   (d) a fluid outlet conduit extending through said second end from said chamber to a fluid outlet port for discharging said fluid from said chamber; and,
   (e) a single helical shaped input fluid flow guide disposed within said chamber and extending longitudinally therein from said first end for a relatively short distance, said input fluid flow guide for imparting input spiral flow momentum to all of said fluid upon entry to said chamber from said fluid inlet conduit.

2. Apparatus as defined in claim 1, wherein said guide extends for about one helical revolution within said chamber.

3. Apparatus for treating fluid with radiant energy from an ultraviolet lamp, said apparatus comprising:
   (a) an outer housing comprising first and second ends and an elongated hollow cylindrical portion extending between said ends peripherally around a longitudinal axis of said cylindrical portion;
   (b) a hollow cylindrical inner housing for housing said lamp, said inner housing being supported by said ends and extending coaxially within said cylindrical portion of said outer housing so as to define an elongated annular chamber between said housings, at least a substantial portion of the length of said inner housing being formed from material sufficiently transmissible to permit ultraviolet energy radiating from said lamp to pass through said inner housing into said chamber and thereby irradiate fluid flowing through said chamber;

(c) a fluid inlet conduit extending through said first end from a fluid inlet port to said chamber for receiving said fluid from an external source of fluid and directing said fluid to said chamber;

(d) a fluid outlet conduit extending through said second end from said chamber to a fluid outlet port for discharging said fluid from said chamber;

(e) a helical shaped input fluid flow guide disposed within said chamber and extending longitudinally therein from said first end for a relatively short distance, said input fluid flow guide for imparting input spiral flow momentum to said fluid upon entry to said chamber from said fluid inlet conduit; and, (f) a helical shaped output fluid flow guide disposed within said chamber relatively far from said input fluid flow guide, said output fluid flow guide extending longitudinally within said chamber from said second end for a relatively short distance, said output fluid flow guide for imparting output spiral flow momentum to said fluid as it approaches discharge from said chamber through said fluid outlet conduit.

4. Apparatus as defined in claim 3, wherein each of said guides extends for about one helical revolution within said chamber.

5. Apparatus as defined in claim 1, wherein said input fluid flow guide comprises a helical ramp having an inner radius, an outer radius, and a ramp surface extending flatly between said inner radius and said outer radius.

6. Apparatus as defined in claim 5, wherein the inner radius of said ramp substantially corresponds to an outer radius of said inner housing and the outer radius of said ramp substantially corresponds to an inner radius of said outer housing.

7. Apparatus as defined in claim 6, wherein said guide extends for about one helical revolution within said chamber.

8. Apparatus as defined in claim 3, wherein:

(a) said input fluid flow guide comprises a first helical ramp characterized by an inner radius of said first helical ramp, an outer radius of said first helical ramp, and a ramp surface of said first helical ramp extending flatly between said inner radius and said outer radius, and;

(b) said output fluid flow guide comprises a second helical ramp characterized by an inner radius of said second helical ramp, an outer radius of said second helical ramp, and a ramp surface of said second helical ramp extending flatly between said inner radius and said outer radius.

9. Apparatus as defined in claim 8, wherein the inner radius of each of said ramps substantially corresponds to an outer radius of said inner housing and the outer radius of each of said ramps substantially corresponds to an inner radius of said outer housing.

10. Apparatus as defined in claim 9, wherein each of said guides extends for about one helical revolution within said chamber.

11. Apparatus as defined in any one or more of the foregoing claims wherein said fluid is potable water.

* * * * *